(12) United States Patent
Hare et al.

(10) Patent No.: US 6,505,126 B1
(45) Date of Patent: Jan. 7, 2003

(54) METHOD TO IDENTIFY FUNGAL GENES USEFUL AS ANTIFUNGAL TARGETS

(75) Inventors: Roberta S. Hare, Gillette, NJ (US); George H. Miller, Menlo Park, CA (US); Karen J. Shaw, Poway, CA (US); George H. Shimer, Jr., Boston, MA (US)

(73) Assignees: Schering-Plough Corporation, Kenilworth, NJ (US); Genome Therapeutics Corporation, Waltham, MA (US)

( * ) Notice: Subject to any disclaimer, the term of this patent is extended or adjusted under 35 U.S.C. 154(b) by 0 days.

(21) Appl. No.: 09/276,361

(22) Filed: Mar. 25, 1999

Related U.S. Application Data

(60) Provisional application No. 60/079,432, filed on Mar. 25, 1998.

(51) Int. Cl.[7] ............ G01N 33/569; C12Q 1/68; C12N 15/66; C07H 21/04
(52) U.S. Cl. ............ 702/20; 435/6; 435/7.31; 435/7.32; 435/7.21; 435/91.1; 435/91.4; 536/23.74
(58) Field of Search ............ 435/6, 7.1, 7.2, 435/7.31, 7.4, 69.9, 7.32, 7.21, 91.1, 91.4; 536/23.1, 23.2, 23.7, 23.74, 24.3; 702/20

(56) References Cited

U.S. PATENT DOCUMENTS

| | | | | |
|---|---|---|---|---|
| 5,612,180 | A | | 3/1997 | Brown et al. ............ 435/6 |
| 5,723,292 | A | * | 3/1998 | Kawasaki et al. ............ 435/6 |
| 5,756,305 | A | * | 5/1998 | Timberlake et al. ............ 435/34 |
| 5,869,290 | A | * | 2/1999 | Freeman et al. ............ 435/69.1 |

OTHER PUBLICATIONS

Burns N, Grimwade B, Ross–Macdonald PB, Choi EY, Finberg K, Roeder GS, Snyder M. Large–scale analysis of gene expression, protein localization, and gene disruption in *Saccharomyces cerevisiae*. *Gene Dev.* May 1994, 1;8(9):1087–105.

Maftahi M, Gaillardin C, Nicaud JM. Generation of *Saccharomyces cerevisiae* deletants and basic phenotypic analysis of eight novel genes from the left arm of chromosome XIV. *Yeast*. 1998 Feb;14(3):271–80.

Chun KT, Goebl MG. The identification of transposon–tagged mutations in essential genes that affect cell morphology in *Saccharomyces cerevisiae*. *Genetics*. 1996 Jan.;142(1):39–50.

Garfinkel DJ. Insertional mutagenesis by Ty elements in *Saccharomyces cerevisiae*. *Methods Mol. Biol.* 1996,53:227–37.

Smith V, Botstein D, Brown PO. Genetic footprinting: a genomic strategy for determining a gene's function given its sequence. *Proc Natl Acad Sci U S A*. 1995 Jul. 3;92(14):6479–83.

Smith V, Chou KN, Lashkari D, Botstein D, Brown PO. Functional analysis of the genes of yeast chromosome V by genetic footprinting. *Science*. 1996 Dec. 20;274(5295):2069–74.

* cited by examiner

*Primary Examiner*—John S. Brusca
*Assistant Examiner*—Majorie A. Moran
(74) *Attorney, Agent, or Firm*—Morgan & Finnegan, LLP

(57) ABSTRACT

The invention provides methods for identifying nucleic acids and polypeptides derived from fungi that are useful as antifungal targets for diagnosis and/or treatment of fungal diseases. The invention also provides isolated fungal-specific nucleic acids and polypeptides comprising antifungal targets. Methods for identifying antifungal agents that interact with and/or alter the function the antifungal targets are provided.

14 Claims, No Drawings

SEQUENCE LISTING

<160> NUMBER OF SEQ ID NOS: 1

<210> SEQ ID NO 1
<211> LENGTH: 25
<212> TYPE: DNA
<213> ORGANISM: Saccharomyces cerevisiae

<400> SEQUENCE: 1
agagctcccg ggatcctcta ctaac                               25

METHOD TO IDENTIFY FUNGAL GENES USEFUL AS ANTIFUNGAL TARGETS

The application claims priority to provisional application Serial No. 60/079,432, filed Mar. 25, 1998.

FIELD OF THE INVENTION

The invention relates to methods for identifying fungal-derived nucleic acids and polypeptides that are useful as molecular targets for diagnosis and treatment of pathological conditions, as well as the isolated nucleic acids and polypeptides themselves. The invention also relates to compositions and methods for the diagnosis, prevention, and amelioration of pathological conditions resulting from fungal infection.

BACKGROUND OF THE INVENTION

Development of effective methods and compositions for the prevention and the treatment of fungal infections is a critical goal of the pharmaceutical and agricultural industries. The major fungal animal pathogens in North America are Candida species and Aspergillus species, as well as *Histoplasma capsulatum, Coccidioides immitis, Blastomyces dermatitidis*, and *Cryptococcus neoformans* (Medically Important Fungi, Second Edition, Davise H. Larone, Ed., American Society for Microbiology, Washington, D.C.).

Fungal infections are a significant and growing health problem, especially in immunocompromised patients. Although several classes of antifungal agents are currently marketed, including compounds such as flucytosine, azoles, allylamines, and amphotericin, all of these agents are limited either by lack of fungicidal activity, toxicity, or development of resistance.

For example, patients suffering from AIDS may contract aspergillosis and endemic infections such as coccidiodomycoses and histoplasmoses. Cancer and transplant patients suffer high morbidity and mortality from opportunistic fungal infections such as those caused by Aspergillus and Fusarium. Furthermore, the development of fungal and yeast strains that are resistant to the above compounds will necessitate the development of antifungals with new mechanisms of action. There is also a need for alternative preventive and therapeutic agents, such as effective vaccines and other immunotherapeutic agents, for the prevention and/or treatment of disease caused by such microorganisms.

SUMMARY OF THE INVENTION

The present invention fulfills this need by providing methods and compositions for identifying nucleic acids and polypeptides derived from fungi that are useful as antifungal targets. The methods are carried out by:
(i) assessing whether a fungal-derived nucleic acid, or a polypeptide encoded therein, is important for viability of the fungal species from which it is derived; and
(ii) determining if the nucleic acid or polypeptide shares substantial homology with any nucleic acids or polypeptides derived from bacterial species, other fungal species, and higher eukaryotic species.

According to the invention, an antifungal target comprises a nucleic acid or polypeptide which
(a) is important for viability of the fungus from which it is derived;
(b) does not share substantial sequence homology with any nucleic acid or polypeptide derived from bacterial or higher eukaryotic species; and
(c) is present in at least one pathogenic fungal species.

The invention also provides libraries of antifungal targets derived from different fungal species, including without limitation *Saccharomyces cerevisiae, Candida albicans, Aspergillus fumigatus, Schizosaccharomyces pombe, Histoplasma capsulatum, Coccidioides immitis, Blastomyces dermatitidis, Cryptococcus neoformans, Paracoccidioides brasiliensis*, and *Pneumocystis carinii*. The libraries may comprise a plurality of isolated nucleic acids, a plurality of isolated polypeptides, or a plurality of bacterial cells, each of which contains a vector comprising a particular nucleic acid and which may also contain the fungal polypeptide encoded therein.

Another aspect of the invention encompasses the use of such fungal specific targets, or fungal specific antibodies, in diagnostic applications.

Still another aspect of the invention encompasses methods for identifying antifungal agents that interact with and/or alter the function either directly or indirectly of the antifungal targets described above. Such methods include without limitation overexpression assays and ligand-binding assays, and are used in low-throughput or high-throughput modes to screen compounds and extracts for antifungal activity, whether fungicidal or fungistatic. In one series of embodiments, the methods comprise: (i) contacting a test compound with an fungal target protein; and (ii) selecting as candidate antifungal agents those test compounds that bind to the protein.

In yet another aspect, the invention encompasses antifungal agents that bind to, or otherwise influence the activity or function of, any of the antifungal target genes or polypeptides of the invention. Antifungal agents may include nucleic acids, particularly antisense oligonucleotides; peptides; oligosaccharides; lipids; derivatives of any of the foregoing, or other molecules.

DETAILED DESCRIPTION OF THE INVENTION

All patent applications, patents, and literature references cited in this specification are hereby incorporated herein by reference in their entirety. In the case of conflict, the present description, including definitions, is intended to control.
Definitions:

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

2. An "open reading frame" (ORF) as used herein is a region of a polynucleotide sequence having a start and stop codon and which may encode a polypeptide. This region may represent a portion of a coding sequence or may comprise a total coding sequence for the polypeptide.

3. A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

4. A "complement" of a nucleic acid sequence as used herein refers to the "antisense" sequence that participates in Watson-Crick base-pairing with the original sequence.

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

7. A "*S. cerevisiae*-derived" nucleic acid or polypeptide sequence may or may not be present in other yeast or fungal species, and may or may not be present in all *S. cerevisiae* strains. This term is intended to refer to the source from which the sequence was originally isolated (e.g., strain S288C). Thus, a *S. cerevisiae*-derived polypeptide as referred to herein may be used, e.g., as a target to screen for a broad spectrum antifungal/antimycotic agent and/or to search for homologous proteins in other organisms.

8. As used herein, "fungi" include myxomycetes, zygomycetes, ascomycotina, basidiomycotina, and deuteromycotina. "Antifungal" and "antimycotic" are used interchangeably to mean agents or treatments that interfere with the growth, function, or reproduction of fungi, including yeast. Such agents may be fungicidal or fungistatic. Mycoses include without limitation systemic mycoses (such as cryptococcoses, histoplasmoses, and blastomycoses); opportunistic mycoses (such as candidiases and aspergilloses); subcutaneous mycoses (such as sporotrichoses and chromoblastomycoses); dermatomycoses; and superficial mycoses. Also included are mycoses in agricultural plants caused by, e.g., *Magnaporthe grisea, Rhizoctonia solanii, Botrytis cinera, Phytophthora infestans*, Cochliobolus species, and Septoria species. (See, e.g., Davis et al., 1973, Microbiology, Harper and Row, N.Y.).

9. A "probe" refers to a nucleic acid or oligonucleotide that forms a hybrid structure with a sequence in a target region due to complementarity of at least one sequence in the probe with a sequence in the target.

10. Nucleic acids are "hybridizable" to each other when at least one strand of nucleic acid can anneal to another nucleic acid strand under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

11. An "immunogenic component" is a moiety that is capable of eliciting a humoral and/or cellular immune response in a host animal.

12. An "antigenic component" is a moiety that binds to its specific antibody with sufficiently high affinity to form a detectable antigen-antibody complex.

13. A "sample" as used herein refers to a biological sample, such as tissue or fluid isolated from an individual (including without limitation plasma, serum, cerebrospinal fluid, lymph, tears, saliva, milk, pus, and tissue exudates and sections) or from in vitro cell culture constituents, as well as samples obtained from the environment or laboratory procedures.

The present invention provides methods for identifying nucleic acids and polypeptides that are useful as targets for diagnosis and/or treatment of fungal diseases. An "antifungal target" according to the invention is a nucleic acid or polypeptide that (i) is important for fungal viability; (ii) is fungal-specific, i.e., does not share substantial sequence homology with any nucleic acid or polypeptide derived from either bacteria or higher eukaryotic species; and (iii) is present in at least one pathogenic fungal species.

As used herein, a "pathogenic" fungal species is one capable of causing infection and/or infestation in animals or plants and for which methods and compositions useful in diagnosis and/or treatment are desired. In one preferred embodiment, a target gene according to the invention is shared among at least two fungal genera, including without limitation Saccharomyces, Candida, Aspergillus, Schizosaccharomyces, Histoplasma, Coccidioides, Blastomyces, and Cryptococcus species.

An "antifungal target polypeptide" as used herein refers to a polypeptide, or fragment thereof, encoded by an antifungal target gene. In practicing the present invention, each of the criteria used to identify antifungal targets is assessed independently, using methods that are described in more detail below. Typically, the genome of a fungal species is first analyzed to select a library of fungal-specific genes, after which genes within this group that are important for fungal viability are identified. Finally, the presence or absence in a pathogenic fungal species of fungal-specific genes that are important for fungal growth is determined. A pathogenic fungal species is a fungal species capable of causing an infection and/or infestation in animals.

The order in which these assessments are made is not critical in practicing the present invention. For example, an antifungal target gene may be identified by first determining its presence in a pathogenic fungal species, followed by the determination that it is important for growth and that it lacks homology with non-fungal species. Irrespective of the order of determination, genes fulfilling all three of the above-listed criteria are selected as candidate antifungal target genes.

The present invention encompasses libraries comprising a plurality of antifungal target genes and corresponding libraries of antifungal target polypeptides encoded therein. The libraries may comprise individual bacterial clones, each comprising a particular fungal nucleic acid sequence, which may or may not express the polypeptide encoded therein. Alternatively, the libraries may comprise a plurality of isolated genes and polypeptides, respectively.

The invention also encompasses screening methods to identify antifungal agents that bind and/or interfere with the function of an antifungal target gene or polypeptide.

Identification of Fungal-Specific Genes

To identify a fungal gene as an antifungal target, the polypeptide sequence encoded by the ORF present within the gene sequence is compared with polypeptide sequences present in protein databases, such as, e.g., GENBANK, SWISS-PROT, PIR, Human Unigene (National Center for Biotechnology Information), to determine if related genes are present in bacterial or higher eukaryotic (i.e., non-fungal) species, e.g., *X. laevis, C. elegans, M. musculus, Rattus norvegicus* and humans.

Any method known in the art may be used to make this determination. Preferably, the BLAST algorithm is used. Altschul et al., 1990, *J. Mol. Biol.* 215:403–410. BLAST identifies local alignments between the candidate antifungal target and the ORF-encoded sequences in the database and predicts the probability of the local alignment occurring by chance.

Typically, the BLAST analysis employs (i) a scoring matrix (such as, e.g., Blossum 62 or PAM 120) to assign a weighted homology value to each residue and (ii) a filtering program(s) (such as SEG or XNU) that recognizes and eliminates highly repeated sequences from the calculation. An appropriate homology cutoff is then determined by performing BLAST comparisons (using a particular scoring matrix and filtering program) between sequences that are known to be related. In this manner, it was established, for example, that BLAST analysis using Blossum 62 and SEG results in P(N) score of less than or equal to $10^{-5}$. It will be understood that other appropriate scoring matrices and filtering programs may be used when the cutoff is calibrated as described herein. That is, the particular cutoff point may vary when different standard parameters are used, but it will correspond to the P(N) scores exhibited when highly related sequences are compared using those particular parameters.

Fungal genes having no substantial homology to any bacterial or higher eukaryotic sequence (as evidenced by, e.g., P(N) scores greater than or equal to $10^{-5}$ when a BLAST comparison is performed using Blossum 62, SEG and XMU as described above) are within the scope of the invention. According to the invention, genes or genomic DNA derived from any fungal species may be analyzed to identify a set of genes derived from that organism that have no orthologs in bacteria or higher eukaryotes.

Identification of Fungal Genes that are Important for Growth/Viability

The present invention encompasses fungal genes that encode polypeptides that are important for viability of the fungal species from which they are derived. As used herein, a gene that is "important for viability" is a gene which, when altered, suppresses fungal viability, growth, and/or reproduction to a detectable extent under at least one growth condition.

The determination that a particular gene is or is not important for growth of a fungal species can be made by examining the effect of deleting and/or disrupting the genes, i.e., by so-called gene "knockout". In this method, homologous recombination is used to replace the genomic copy of a gene with an altered copy containing insertions, deletions, and/or substitutions within the gene such that cells carrying the altered copy do not produce a functional product of the targeted gene. Typically, gene disruption is performed in a diploid fungal cell, or in a haploid cell containing a second copy of the gene being disrupted (such as, e.g., on an autonomously replicating plasmid). Following replacement of the chromosomal copy with the altered gene, viability, growth, and/or replication are monitored, typically in a haploid cell containing only the disrupted, and not the wild-type, version of the gene. Gene disruption can result in cells that are (i) not viable under all or particular growth conditions; (ii) grow more slowly; or (iii) are unaffected, i.e., grow and reproduce at rates similar to wild-type cells. As used herein, a gene is "important for viability" if disruption of the gene results in non-viable or slower-growing cells relative to wild-type cells.

Another means for determining whether a gene is important for viability involves the ability to isolate conditional lethal mutants (such as temperature sensitive mutants) in the specific gene.

Alternatively, genetic footprinting can be used to identify genes that are important for fungal viability (Smith et al., 1995, *Proc. Natl. Acad. Sci. USA* 92:5479–6433; Smith et al., 1996, *Science* 274:2069; U.S. Pat. No. 5,612,180). In genetic footprinting, transposon-mediated insertional mutagenesis is used to insert a predetermined nucleic acid sequence randomly throughout the genome of a cell; this is followed by growth of the mutagenized culture over multiple generations. Finally, each gene of interest is evaluated to determine whether the mutagenized culture contains the transposon inserted into the gene. Genes that are important for viability do not tolerate transposon insertions, while genes that are dispensable or redundant are more likely to tolerate transposon insertions.

Those *S. cerevisiae* genes now discovered to be fungal specific have further been tested for importance to viability using genetic footprinting. Briefly, haploid fungal cells are transformed by a plasmid containing a Ty element, preferably Ty1, under the control of a regulatable promoter. Cells are incubated under conditions in which Ty1 transposase expression is induced. A sample of this culture is removed and genomic DNA is extracted; this is termed the "T0" sample. The culture is then grown for at least 15 population doublings, preferably 20, after which genomic DNA is extracted; this is termed the "T20" sample. Finally, individual genes in the T0 and T20 genomic DNA samples are analyzed using polymerase chain reaction to determine the extent and location of Ty1 insertions (PCR). The number of Ty1 insertions into the open reading frame of a particular gene is quantified and compared between the T0 and T20 samples.

In this way, genetic footprinting identifies genes that may play different roles in growth, which fall into one of the following categories:

Category 1: Genes in which 90–100% of the Ty1 insertions present in the T0 sample have disappeared in the T20 sample.

Category 2: Genes in which >70% and <90% of the Ty1 insertions present in the T0 sample have disappeared in the T20 sample, or in which a large segment of the open reading frame is devoid of Ty1 insertions in the T20 sample relative to the T0 sample.

Category 3: Genes in which 25–70% of the Ty1 insertions present in the T0 sample have disappeared in the T20 sample, or in which some of the Ty1 insertions have decreased in intensity in the T20 sample relative to the T0 sample.

Category 4: Genes in which <25% of the Ty1 insertions present in the T0 sample have disappeared in the T20 sample.

Genes exhibiting footprinting characteristics falling within categories 1 and 2 are designated herein as being "important for viability." Table 1 lists all of the gene names and GenBank Accession No. of targets which (a) are fungal specific and (b) are important to viability, as newly determined by footprinting as described above (i.e., category 1 or 2), and/or are reported in the literature to be important for growth, based on, e.g., prior art footprinting, site-directed gene knockouts, isolation of conditional lethals, etc.

TABLE 1

| Gene Name | Accession No. | Footprinting Category |
|---|---|---|
| YBR078W | 536336 | 2 |
| YBR102C | 536386 | 1 |
| **YBR106W | 536394 | 2 |
| YBR266C | 536698 | 1 |
| YCL062W | 5297 | 1 |
| YCR044C | 5418 | 1 |
| *YCR046C | 5422 | 2 |
| YDL062W | 1431068 | 1 |
| YDL068W | 1431079 | 1 |
| YDL088C | 1431116 | 1 |
| **YDL170W | 1431272 | 1 |
| YDR016C | 840869 | 1 |
| YDR072C | 577799 | 2 |
| YDR118W | 747892 | 1 |
| YDR132C | 665664 | 2 |
| **YDR184C | 1289301 | 2 |
| YDR186C | 1289303 | 2 |
| YDR198C | 755791 | 2 |
| YDR206W | 1122334 | 1 |
| YDR288W | 1332636 | 1 |
| YDR296W | 849216 | 2 |
| YDR318W | 914996 | 1 |
| YDR462W | 927728 | 2 |
| YDR472W | 927742 | 1 |
| YDR494W | 927743 | 2 |
| YFL010C | 836744 | 2 |
| YIL104C | 763242 | 1 |
| *YJL090C | 1008260 | 1 |
| YJL096W | 1008272 | 1 |
| YJL148W | 1015563 | 1 |
| YJR080C | 1015768 | 1 |
| YJR120W | 1015843 | 1 |
| YJR136C | 1015874 | 1 |
| *YER002W | 603594 | 1 |
| *YER008C | 603600 | 1 |
| *YER018C | 603610 | 1 |
| *YER038C | 603271 | 1 |
| *YER104W | 603342 | 2 |
| YGL020C | 1322485 | 1 |
| YGL088W | 1322615 | 2 |
| YGL250W | 1322925 | 2 |
| YGR076C | 1323105 | 1 |
| YGR102C | 1323157 | 2 |
| YGR272C | 1323495 | 1 |
| YKL014C | 486001 | 1 |
| YKL052C | 486073 | 2 |
| YKL098W | 486163 | 2 |
| YKL108W | 486181 | 1 |
| YKL176C | 486310 | 1 |
| **YKR042W | 486485 | 2 |
| YKR100C | 486597 | 2 |
| YLL014W | 1360183 | 1 |
| YLR052W | 1360390 | 2 |
| YLR064W | 1360412 | 2 |
| YLR084C | 1360451 | 1 |
| YLR132C | 1360545 | 1 |
| YLR360W | 609415 | 2 |
| YML020W | 575699 | 2 |
| *YML048W | 642307 | 1 |
| YML114C | 798886 | 1 |
| *YMR064W | 763011 | 1 |
| *YMR168C | 825573 | 1 |
| YNL056W | 1301927 | 2 |
| YNL074C | 1301961 | 1 |
| YNL094W | 1302000 | 2 |
| YNL120C | 1302047 | 1 |
| YNL140C | 1302086 | 2 |
| YNL166C | 1302138 | 2 |
| YNL228W | 1302249 | 1 |
| YNL282W | 1302355 | 2 |
| YNR004W | 1302475 | 2 |
| ***YNR026C | 1302517 | 4 |
| YOL032W | 1419823 | 2 |
| YOL050C | 1419857 | 2 |
| **YOL110W | 1419977 | 2 |
| YOL144W | 1420044 | 1 |
| YOR042W | 1420167 | 1 |

TABLE 1-continued

| Gene Name | Accession No. | Footprinting Category |
|---|---|---|
| YOR050C | 1420183 | 2 |
| YOR144C | 1420366 | 2 |
| YOR170W | 1420416 | 1 |
| YOR172W | 1420419 | 1 |
| YOR219C | 1420506 | 1 |
| *YOR340C | 1420739 | 1 |
| YPL066W | 1079676 | 2 |
| YPL228W | 1370472 | 1 |
| YPL238C | 1370490 | 1 |
| YBR075W | 536330 | 2 |
| YBR099C | 536381 | 2 |
| YBR107C | 536375 | 1 |
| *YBR211C | 536594 | 1 |
| YBR255W | 536677 | 2 |
| *YBR279W | 536722 | 1 |
| YCL007C | 5362 | 1 |
| YCL013W | 5355 | 1 |
| YCL041C | 5322 | 1 |
| YDL013W | 1430977 | 2 |
| YDL107W | 1431152 | 2 |
| YDL139C | 1431215 | 2 |
| YDL151C | 1431237 | 1 |
| YDL209C | 1431348 | 1 |
| *YDL235C | 1431398 | 1 |
| YDR027C | 642299 | 1 |
| YDR161W | 899408 | 1 |
| YDR175C | 1289290 | 1 |
| YDR361C | 849182 | 1 |
| YDR363W | 849171 | 1 |
| YDR499W | 927769 | 1 |
| **YEL045C | 603633 | 1 |
| *YEL053C | 603626 | 2 |
| *YEL055C | 603263 | 1 |
| **YER033C | 603266 | 2 |
| *YER059W | 603295 | 1 |
| **YER161C | 603401 | 2 |
| YFL007W | 836747 | 2 |
| *YFL031W | 836723 | 2 |
| YGL007W | 1322459 | 1 |
| YGL057C | 1322556 | 1 |
| YGR017W | 1322984 | 2 |
| ***YGR147C | 1323248 | 3 |
| YIL039W | 763307 | 1 |
| YJL019W | 1006738 | 1 |
| *YJL025W | 1008140 | 2 |
| *YJL085W | 1008254 | 1 |
| **YJL117W | 1008308 | 1 |
| YJR023C | 1015661 | 2 |
| YJR089W | 1015782 | 2 |
| YJR111C | 1015826 | 2 |
| YLR091W | 1360465 | 1 |
| *YLR105C | 1360492 | 1 |
| YLR181C | 577213 | 2 |
| YLR201C | 544522 | 1 |
| YLR363C | 609418 | 2 |
| YNL051W | 1301913 | 2 |
| *YNL103W | 1302018 | 1 |
| YNL119W | 1302048 | 1 |
| *YNL131W | 1302070 | 2 |
| YNL149C | 1302106 | 1 |
| YOL137W | 1420030 | 1 |
| YPL005W | 965088 | 1 |
| *YPL057C | 1079685 | 2 |
| YPL083C | 1147611 | 1 |
| YPL125W | 1163089 | 1 |
| YPL173W | 1370365 | 2 |
| YPL193W | 1370403 | 1 |
| *YNL216W | 1302229 | 1 |
| *YMR220W | 887601 | 2 |
| *YKL186C | 486329 | 1 |
| ***YKL004W | 485991 | 4 |
| *YLR078C | 1360397 | 1 |
| ***YGR186W | 1323330 | 3 |
| *YDR052C | 798904 | 2 |
| ***YDR478W | 927733 | 4 |
| *YOL069W | 1419893 | 1 |
| YOR030W | 1420145 | 2 |

TABLE 1-continued

| Gene Name | Accession No. | Footprinting Category |
|---|---|---|
| *YGL145W | 1322726 | 2 |
| YGR198W | 1323353 | 1 |
| *YER022W | 603614 | 1 |
| YKR064W | 486531 | 2 |
| *YMR005W | 728652 | 1 |
| *YMR149W | 606448 | 1 |
| YNL152W | 1302110 | 1 |
| *YAL033W | 595552 | 1 |
| *YBR193C | 536559 | 1 |
| *YBR253W | 536673 | 2 |
| YDL121C | 1431179 | 2 |
| YDL157C | 1431249 | 2 |
| YDR003W | 642808 | 1 |
| *YDR079W | 577806 | 2 |
| *YDR137W | 665670 | 2 |
| **YDR329C | 915004 | 1 |
| YDR335W | 1230662 | 2 |
| *YHR052W | 488163 | 1 |
| YDR474C | 927751 | 2 |
| YGL134W | 1322704 | 2 |
| YGL186C | 1322803 | 2 |
| *YGR036C | 1323019 | 2 |
| YOL076W | 1419907 | 1 |
| *YPL076W | 1147617 | 1 |
| YPL142C | 1370306 | 1 |
| YPR100W | 914971 | 1 |
| YDR063W | 798914 | 1 |
| YJR118C | 1015839 | 2 |
| YJL084C | 1008250 | 2 |
| *YJR122W | 1015847 | 1 |
| YBR108W | 536379 | 2 |
| *YJR112W | 1015828 | 1 |
| **YOR188W | 1420451 | 2 |
| YOR146W | 1420369 | 1 |
| YOR078W | 1420237 | 1 |
| YOL036W | 1419830 | 1 |
| YNL306W | 1302405 | 1 |
| YMR212C | 854464 | 1 |
| YMR100W | 854437 | 2 |
| YMR086W | 807968 | 1 |
| YMR032W | 798957 | 2 |
| *YKR050W | 486503 | 2 |
| YLR068W | 1360420 | 1 |
| YJR082C | 1015770 | 2 |
| YDR180W | 1289297 | 2 |
| YDR162C | 899409 | 2 |
| YIR010W | 763355 | 1 |
| YDR068W | 798919 | 2 |
| YDL202W | 1431334 | 1 |
| YDL196W | 1431322 | 2 |
| YPR020W | 887598 | 1 |
| YGL023C | 1322491 | 2 |
| *YGL225W | 1322877 | 1 |
| YGR013W | 1322976 | 1 |
| YGR089W | 1323131 | 2 |
| YKR019C | 486439 | 2 |
| *YLR071C | 1360426 | 2 |
| YLR177W | 577202 | 2 |
| YLR187W | 577196 | 2 |
| YLR219W | 544498 | 1 |
| *YLR223C | 609372 | 1 |
| YML009C | 854481 | 2 |
| YML117W | 798883 | 2 |
| YMR193W | 642285 | 1 |
| YNL091W | 1301994 | 2 |
| *YNL251C | 1302295 | 1 |
| *YNL261W | 1302315 | 1 |
| **YBL103C | 536174 | 2 |
| *YDL153C | 1431240 | 1 |
| **YDL181W | 1431293 | 2 |
| YDR119W | 747893 | 2 |
| YDR233C | 728688 | 2 |
| *YDR381W | 849202 | 1 |
| YDR468C | 927753 | 1 |
| YFR003C | 836758 | 1 |
| *YHR101C | 529128 | 2 |
| YHR151C | 500662 | 2 |

TABLE 1-continued

| Gene Name | Accession No. | Footprinting Category |
|---|---|---|
| *YHR187W | 458936 | 2 |
| **YIL049W | 763297 | 2 |
| *YPR060C | 805040 | 2 |
| *YKL038W | 486046 | 2 |
| ****YKL112W | 486187 | |
| ****YAL043C | 595541 | |
| ****YDL150W | 1431238 | |
| ****YJL061W | 1008207 | |
| ****YDL105W | 1431148 | |
| ****YOR329C | 1420719 | |
| ****YDR498C | 927768 | |
| ****YDR464W | 927729 | |
| ****YDR443C | 927709 | |
| ****YBL034C | 536043 | |
| ****YBR156C | 536488 | |
| ****YKL089W | 486133 | |
| ****YOR098C | 1420275 | |
| ****YHR118C | 529137 | |
| ****YNL272C | 1302336 | |
| ****YGR140W | 1323234 | |
| ****YIR011C | 763356 | |
| ****YML104C | 798896 | |
| ****YGL122C | 1322681 | |
| ****YGL172W | 1322776 | |
| ****YHR083W | 500828 | |
| ****YMR094W | 349181 | |
| ****YLR233C | 609378 | |
| ****YNL151C | 1302108 | |
| ****YHR036W | 488173 | |
| *YHR197W | 458930 | 1 |
| ****YIL150C | 763196 | |
| ****YNL188W | 1302177 | |
| ****YJL173C | 1008369 | |
| ****YPR190C | 786307 | |
| ****YPR055W | 805036 | |
| *YOR149C | 1420375 | 2 |
| ****YOR075W | 1420231 | |
| ****YHR178W | 458893 | |
| ****YHR196W | 458944 | |
| ****YHR085W | 500826 | |
| *YAL002W | 349749 | 2 |
| YAL056W | 623256 | 2 |
| YBL077W | 536122 | 2 |
| YBL083C | 536133 | 2 |
| YBR004C | 536192 | 1 |
| YBR030W | 536242 | 1 |
| YBR043C | 536268 | 1 |
| YBR064W | 536308 | 2 |
| YBR101C | 536384 | 1 |
| *YBR123C | 536406 | 1 |
| YBR167C | 536508 | 1 |
| **YDL020C | 1430990 | 1 |
| YDL032W | 1431013 | 1 |
| YDL034W | 1431016 | 1 |
| YDL065C | 1431072 | 1 |
| *YDL207W | 1431344 | 1 |
| YDR065W | 798916 | 1 |
| *YDR082W | 577809 | 1 |
| YDR141C | 665674 | 1 |
| *YEL035C | 603644 | 2 |
| *YER032W | 603624 | 2 |
| YFL024C | 836730 | 1 |
| YGL069C | 1322578 | 2 |
| YGL113W | 1322663 | 1 |
| YGL247W | 1322919 | 1 |
| YGR057C | 1323071 | 1 |
| YGR071C | 1323097 | 2 |
| *YGR099W | 1323151 | 1 |
| YGR113W | 1323183 | 2 |
| YGR196C | 1323349 | 2 |
| YGR215W | 1323387 | 2 |
| YIL019W | 763327 | 2 |
| YJL204C | 1008426 | 2 |
| **YJR075W | 1015760 | 2 |
| YKL046C | 486062 | 1 |
| **YKR006C | 486413 | 1 |
| YKR022C | 486445 | 2 |

TABLE 1-continued

| Gene Name | Accession No. | Footprinting Category |
|---|---|---|
| YLR190W | 577194 | 1 |
| *YLR256W | 662331 | 2 |
| YLR373C | 609420 | 2 |
| *YML031W | 575688 | 1 |
| YML034W | 575685 | 2 |
| YMR185W | 854455 | 2 |
| YNL080C | 1301973 | 2 |
| YNL310C | 1302413 | 1 |
| YOR322C | 1420706 | 2 |
| YOR350C | 1420762 | 2 |
| *YPL011C | 965082 | 1 |
| YPL124W | 1163090 | 2 |
| *YPL255W | 1370524 | 2 |
| YPR042C | 1370299 | 1 |
| ***YMR059W | 817892 | 3 |
| ***YCR035C | 5408 | 3 |
| ***YBL018C | 536011 | 4 |
| ***YCL052C | 5309 | 3 |
| ***YDR201W | 755793 | 3 |
| ***YHR143W-A | 2358017 | 3 |
| ***YDR362C | 849183 | 3 |
| *YAL001C | 385245 | 1 |
| ***YLR127C | 1360535 | 3 |
| ***YOR249C | 1420565 | 3 |
| **YBR038W | 536258 | 1 |
| ****YML043C | 642312 | |
| ****YLL004W | 1360163 | |
| ****YGR030C | 132008 | |
| ****YIR015W | 763360 | |
| ****YOR174W | 1420423 | |
| ****YDR088C | 577815 | |
| ****YKR063C | 486529 | |
| ****YDR420W | 927691 | |
| ****YJL087C | 1008252 | |
| ****YPL085W | 1147609 | |
| ****YJL042W | 1008169 | |
| ****YMR197C | 642290 | |
| ****YJL054W | 1008193 | |
| ****YKR037C | 486475 | |
| ****YMR117C | 817877 | |
| ****YBR091C | 536361 | |
| ****YGL061C | 1322564 | |
| ****YGL075C | 1322589 | |
| ****YJR067C | 1015745 | |
| ****YKL165C | 486289 | |
| ****YLR144C | 1360568 | |
| ****YLR336C | 609391 | |
| ****YBL093C | 536154 | |
| ****YIL004C | 763342 | |
| ****YPL128C | 1244785 | |
| ****YML046W | 642309 | |
| ****YDR182W | 1289299 | |
| ****YDR393W | 927326 | |
| ****YOR110W | 1420297 | |
| ****YGR075C | 1323103 | |
| ****YNL039W | 1301890 | |
| ****YAL034W-A | 1326057 | |
| ****YDR053W | 1431495 | |
| ****YDR407C | 927338 | |
| ****YDR412W | 927689 | |
| ****YDR434W | 927700 | |
| ****YLL035W | 1360224 | |
| ****YLR037W | 1360226 | |
| ****YLR010C | 1360304 | |
| ****YLR101C | 1360484 | |
| ****YMR281W | 825547 | |
| ****YMR298W | 530355 | |
| ****YNL258C | 1302309 | |
| ****YOL026C | 1419811 | |
| ****YPL126W | 1163088 | |
| ****YDR240C | 817826 | |
| ****YJR141W | 1015884 | |
| ****YLL003W | 1360161 | |
| ****YNL038W | 1301888 | |
| ****YBR049C | 536280 | |
| ****YGL228W | 1322883 | |
| ****YNL194C | 1302189 | |

TABLE 1-continued

| Gene Name | Accession No. | Footprinting Category |
|---|---|---|
| ****YJR041C | 1015693 | |
| ****YJR046W | 1015703 | |
| ****YML091C | 575712 | |

Genes listed in Table 1 which carry 0–3 asterisks have been newly footprinted and categorized as described herein.

Genes listed in Table 1 which lack any asterisk(s) have now been newly discovered to be important for viability (footprint category 1 or 2).

Genes designated in Table 1 with one asterisk (*) have been reported in the published literature as being important for viability, which reports have now been confirmed by footprinting (footprint category 1 or 2). Table 2 lists these genes Genes designated in Table 1 with two asterisks (**) were classified into footprint category 1 or 2, a finding contrary to the published literature. Table 3 lists these genes.

Genes designated in Table 1 with three asterisks (***) were classified into footprint category 3 or 4. Published literature, however, indicates importance for viability. Table 4 lists these genes.

Genes designated in Table 1 with four asterisks (****) have been reported in the published literature as important for viability. Footprinting and categorization of these genes was not undertaken. Table 5 lists these genes.

An inspection of the information set forth in Tables 2–5 will show that information for some genes as to their importance for cell viability was obtained from an Internet web site(s). Specifically, Stanford Genome Database (Stanford University, Stanford, Calif. 94305), Yeast Proteome Database (Proteome, Inc., 100 Cummings Center, Suite 435M, Beverly, Mass. 01915), Washington University (St. Louis, Mo.), MIPS (Munich Information Centre for Protein Sequences, Max-Planck-Institue für Biochimie, Am Klopferspitz 18a, 82152 Martinsried, Germany), and/or Research Genetics, Inc. (Research Genetics, Inc., 2130 Memorial Parkway, SW, Huntsville, Ala. 35801). It will be understood by those skilled in the art that this information has been published on these web sites prior to written publication, e.g., in a scientific journal. Subsequent written publication of this information can be easily obtained by one skilled in the art by a routine search of the published literature using the information disclosed herein.

Among the genes listed in Table 1, genes YNL261W, YHR118C and YLL004W (U.S. Pat. Nos. 5,589,341 and 5,614,618) and gene YPL011C (Published International Application No. WO 95/09390) have been disclosed in the art as useful targets for antifungal agents. The use of YNL261W, YHR118C, YLL004W and YPL011C sequences as targets is not encompassed by the screening methods described herein. Libraries of targets comprising YNL261W, YHR118C, YLL004W and YPL011C sequences, as well as libraries of targets specifically excluding these sequences are, however, included within the scope of the invention. The use of the *C. alvicans* homolog of YJR067C has also been disclosed in the art as a useful target for antifungal agents (U.S. Pat. No. 5,869,290). The specific use of use of the *C. alvicans* YJR067C homolog as a target in the sceening method described herein is disclaimed, its inclusion as a member of a library of targets is encompassed by the invention.

TABLE 2

(*)

| Gene Name | Reference |
|---|---|
| YCR046C | Yeast, 12: 577–582. |
| YJL090C | Proc. Natl. Acad. Sci., USA 92:11791–11795. |
| YER002W | Science, 274: 2069–2074. |
| YER008C | Science, 274: 2069–2074. |
| YER018C | Science, 274: 2069–2074. |
| YER038C | Science, 274: 2069–2074. |
| YER104W | Science, 274: 2069–2074. |
| YML048W | Stanford Genome Database [genome-world wide web.stanford.edu/Saccharomyces/]. |
| YMR064W | Curr. Genet., 24: 126–35 (1993). |
| YMR168C | EMBO J., 13:5203–5211. |
| YOR340C | J Biol Chem., 270: 24252–24257. |
| YBR211C | Genetics 142: 39–50. |
| YBR279W | Mol. Cell. Biol., 16: 669–676. |
| YDL235C | Cell 86:865–875. |
| YEL053C | Science, 274: 2069–2074. |
| YEL055C | Science, 274: 2069–2074. |
| YER059W | Science, 274: 2069–2074. |
| YFL031W | Nucleic Acids Res., 22:5279–5288. |
| YJL025W | Genes and Dev. 8:2349–2362. |
| YJL085W | EMBO J., 15: 6483–6494. |
| YLR105C | Cell, 89:849–858. |
| YNL103W | Stanford Genome Database [genome–world wide web. stanford. edu/Saccharomyces/]. Yeast Proteome Database [quest 7.proteome.com/YPD]. |
| YNL131W | Mol. Cell. Biol., 1555:3382. |
| YPL057C | Mol. Gen. Genet., 246, 269–281. |
| YNL216W | Cell, 51:721–732. |
| YMR220W | Mol. Cell. Biol., 11: 620–631. |
| YKL186C | Mol. Biol. Cell., 5: 1253–1263. |
| YLR078C | Cell, 73: 735–745. |
| YDR052C | Science, 265: 1243–1246. |
| YDL069W | J. Cell. Biol., 125: 853–866. |
| YGL145W | EMBO J., 12:2831–2840. |
| YER022W | Cell, 73:1361–1375. |
| YMR005W | Yeast Proteome Database [quest 7.proteome.com/YPD]. |
| YMR149W | EMBO J. 12:279–284. |
| YAL033W | J. Mol. Biol., 225:53–65. |
| YBR193C | Yeast, 9: 645–659. |
| YBR253W | Cell, 73 1361–1375. |
| YDR079W | J. Biol. Chem., 271:18499–18507. |
| YDR137W | Nucleic Acids Res., 18: 1064. |
| YHR052W | By footprint (Stanford U.) and disruption (Washington U.). uniform resource locator: [hypertext transfer protocol:genome.wustl.edu/gsc/yeast/chromosome8ORFs.html]. |
| YGR036C | Stanford Genome Database [genome–world wide web.stanford.edu/Saccharomyces/]. Yeast Proteome Database [quest 7.proteome.com/YPD]. |
| YPL076W | Yeast, 11: 1093–101. |
| YJR122W | Stanford Genome Database [genome–world wide web.stanford.edu/Saccharomyces/]. Yeast Proteome Database [quest 7.proteome.com/YPD]. |
| YKR050W | Genetics, 125:305–312. |
| YGL225W | Genetics, 140:933–943. |
| YLR071C | Mol. Cell. Biol., 10:4130–4138. |
| YLR223C | Yeast, 11:261–270. |
| YNL251C | Mol. Cell. Biol., 16:6993–7003. |
| YNL261W | Cell, 51:667–676. U.S. Pat. Nos. 5,589,341 and 5,614,618. |
| YDL153C | Stanford Genome Database [genome–world wide web.stanford.edu/Saccharomyces/]. Yeast Proteome Database [quest 7.proteome.com/YPD] |
| YDR381W | RNA, 3:527–537. |
| YHR101C | By disruption at Washington University [hypertext transfer protocol:genome.wustl.edu/gsc/yeast/chromosome8ORFs.html]. |
| YHR187W | Biosci. Biotechnol. Biochem., 61:704–709. |
| YPR060C | Yeast Proteome Database [quest 7.proteome.com/YPD]. |
| YKL038W | Mol. Cell. Biol., 16:6419–6426. |
| YHR197W | By disruption at Washington University [hypertext transfer protocol:genome.wustl.edu/gsc/yeast/chromosome8ORFs.html]. |
| YOR149C | Mol. Gen. Genet., 225:257–265. |
| YAL002W | J. Biol. Chem., 271:33607–33615. |

TABLE 2-continued (*)

| Gene Name | Reference |
|---|---|
| YBR123C | Proc. Natl. Acad. Sci., USA 88(11):4887–4891. |
| YDL207W | Nature, 383:357–360. |
| YDR082W | Genes Dev., 11:512–527. |
| YEL035C | Science 274: 2069–2074. |
| YER032W | Science 274: 2069–2074. |
| YGR099W | Mol. Cell. Biol. 16:3094–105. |
| YLR256W | Stanford Genome Database [genome-world wide web. stanford.edu/Saccharomyces/]. Yeast Proteome Database [quest 7.proteome.com/YPD]. |
| YML031W | J. Cell Biol., 122: 743–751. |
| YPL011C | Nature, 383: 185–188. WO 95/09390 |
| YPL255W | Genetics 144: 979–989. |
| YAL001C | Proc. Natl. Acad. Sci. USA, 89:10512–10516. |

TABLE 3

(**)

| Gene Name | Reference |
|---|---|
| YBR106W | Mol. Gen. Genet., 1996, 251(5):580–590. |
| YDL170W | Mol. Gen. Genet., 220: 269–276. |
| YDR184C | Yeast Proteome Database [quest 7.proteome.com/YPD]. |
| YKR042W | Yeast, 12:623. |
| YOL110W | Mol. Cell. Biol. 15:1333–1342. |
| YEL045C | Science, 274: 2069–2074. |
| YER033C | Science, 274: 2069–2074. |
| YER161C | Science, 274: 2069–2074. |
| YJL117W | Mol. Gen. Genet., 251: 580–590. |
| YDR329C | J. Cell. Biol., 114: 1167–1178. |
| YOR188W | Mol. Cell. Biol., 11:1295–1305. |
| YBL103C | Mol. Cell. Biol., 17:1110–1117. |
| YDL181W | J. Biol. Chem., 265:6274–6278. |
| YIL049W | Genetics, 145:671–684. |
| YDL020C | Genetics, 134:159–173. |
| YJR075W | Genetics, 145: 637–45. |
| YKR006C | Yeast Proteome Database [quest 7.proteome.com/YPD]. |
| YBR038W | Proc. Natl. Acad. Sci. USA, 87:7424–7428. |

TABLE 4

(***)

| Gene Name | Reference |
|---|---|
| YNR026C | J. Cell. Biol., 107:851–863. |
| YGR147C | J. Biol. Chem., 269:13141–13147. |
| YKL004W | Mol. Gen. Genet., 251:236–244. |
| YGR186W | Proc. Natl. Acad. Sci. USA 92:3127–3131. |
| YDR478W | Genes & Dev. 8:2617–2628. |
| YMR059W | Cell, 89:849–858. |
| YCR035C | Cell, 91:457–466. |
| YBL018C | Genes Dev., 12:1678–1690. |
| YCL052C | Genetics 149:1277–1291. |
| YDR201W | J. Cell Biol., 141:967–977. |
| YHR143W-a | hypertext transfer protocol:world wide web.mips.biochem.mpg.de/proj/yeast/tables/essential/index.html |
| YDR362C | Mol. Cell. Biol., 18:1–9. |
| YLR127C | Science, 279:1219–1222. |
| YOR249C | Science, 279:1219–1222. |

TABLE 5

(****)

| Gene Name | Reference |
|---|---|
| YKL112W | Genes Dev., 3:1926–1939. |
| YAL043C | Mol. Cell. Biol., 12:3843–3856. |
| YDL150W | Mol. Cell. Biol., 12:4314–4326. |
| YJL561W | J. Cell Biol. 130:1275–1281. |
| YDL105W | Yeast, 10:1653 –1656. |
| YOR329C | Mol. Biol. Cell., 7:245–260. |
| YDR498C | EMBO J., 11:423–432. |
| YDR464W | Genetics, 136:833–847. |
| YDR443C | Genes Dev., 9:897–910. |
| YBL034C | J. Cell Biol., 127:1973–1984. |
| YBR156c | Yeast, 11:865–871. |
| YKL089W | J. Cell Biol., 123:387–403. |
| YOR098C | Cell, 61:965–978. |
| YHR118C | Science, 262:1870–1874. U.S. Pat. Nos. 5,589,341 and 5,614,618 |
| YNL272C | J. Cell Biol., 110:1897–1909. |
| YGR140W | J. Cell Biol., 121:513–519 |
| YIR011C | Mol. Cell. Biol., 14:6350–6360. |
| YML104C | J. Cell Biol., 111:967–976. |
| YGL122C | Mol. Cell. Biol., 13:2730–2741. |
| YGL172W | J. Cell Biol., 119:705–723. |
| YHR083W | Essential by disruption at Washington University [hypertext transfer protocol:genome.wustl.edu/gsc/yeast/chromosome8ORFs.html]. |
| YMR094W | Cell, 73:761–774. |
| YLR233C | Cell, 57:633–643. |
| YNL151C | Mol. Cell. Biol., 10:4737–4743. |
| YHR036W | Essential by disruption at Washington University [hypertext transfer protocol:genome.wustl.edu/gsc/yeast/chromosome8ORFs.html]. |
| YIL150C | Yeast, 8:273–289. |
| YNL188W | Cell, 48:1047–1060. |
| YJL173C | Genes Dev., 5:1589–1600. |
| YPR190C | Mol. Cell. Biol. 12:4433–4440. |
| YPR055W | J. Cell. Biol. 119:1041–1056. |
| YOR075W | Curr. Genet., 30:396–403. |
| YHR178W | Essential by disruption at Washington University [hypertext transfer protocol:genome.wustl.edu/gsc/yeast/chromosome8ORFs.html]. |
| YHR196W | Essential by disruption at Washington University [hypertext transfer protocol:genome.wutsl.edu/gsc/yeast/chromosome8ORFs.html]. |
| YHR085W | Essential by disruption at Washington University [hypertext transfer protocol:genome wustl.edu/gsclyeast/chromosome8ORFs.html]. |
| YML043C | J. Bio. Chem., 271:21062–21067. |
| YLL004W | Cell, 88:493–502. U.S. Pat. Nos. 5,589,341 and 5,614,618. |
| YgR030C | Genes Dev., 12:1678–90. |
| YIR015W | Genes Dev., 12:1678–90. |
| YOR174W | Genes Dev., 12:45–54. |
| YDR088C | Genes Dev., 6:2112–24. |
| YKR063C | Genetics, 141:857–871. |
| YDR420W | J. Bacteriol., 176:1488–1499. |
| YJL087C | J. Biol. Chem., 267:4577–4582. |
| YPL085W | J. Cell Biol., 131:311–324. |
| YJL042W | J. Cell Biol., 135:1323–1339. |
| YMR197C | J. Cell Biol., 137:1511–1524. |
| YJL054W | J. Cell Biol., 139:1663–1675. |
| YKR037C | J. Cell Biol., 141:967–977. |
| YMR117C | J. Cell Biol., 141:967–977. |
| YBR091C | J. Biol. Chem., 271:17219–17225. |
| YGL061C | J. Cell Biol., 143:1029–1040. |
| YCL075C | hypertext transfer protocol:world wide web/mips.biochem.mpg.de/proj/yeast/tables/essential/index.html |
| YJR067C | hypertext transfer protocol:world wide web/mips.biochem.mpg.de/proj/yeast/tables/essential/index.html |
| YKL165C | hypertext transfer protocol:world wide web/mips.biochem.mpg.de/proj/yeast/tables/essential/index.html |
| YLR144C | hypertext transfer protocol:world wide web/mips.biochem.mpg.de/proj/yeast/tables/essential/index.html |
| YLR336C | hypertext transfer protocol:world wide web/mips.biochem.mpg.de/proj/yeast/tables/essential/index.html |
| YBL093C | Mol. Cell. Biol., 11:5639–5647. |
| YIL004C | Mol. Cell. Biol., 11:872–885. |
| YPL12BC | Mol. Cell. Biol., 13:1306–1314. |
| YML046W | Mol. Cell. Biol., 14:3623–2633. |
| YDR182W | Mol. Cell. Biol., 14:8037–8050. |
| YDR393W | Mol. Cell. Biol., 18:1–9. |
| YOR110W | Mol. Cell. Biol., 18:1391–3200. |
| YGR075C | Mol. Cell. Biol., 12:3939–3947 |
| YNL039W | Proc. Natl. Acad. Sci. USA 92:9786–9790. |
| YAL034W-A | Research Genetics, Inc. [world wide web.resgen.com] |
| YDR053W | Research Genetics, Inc. [world wide web.resgen.com] |
| YDR407C | Research Genetics, Inc. [world wide web.resgen.com] |
| YDR412W | Research Genetics, Inc. [world wide web.resgen.com] |
| YDR434W | Research Genetics, Inc. [world wide web.resgen.com] |
| YLL035W | Research Genetics, Inc. [world wide web.resgen.com] |
| YLL037W | Research Genetics, Inc. [world wide web.resgen.com] |
| YLR010C | Research Genetics, Inc. [world wide web.resgen.com] |
| YLR101C | Research Genetics, Inc. [world wide web.resgen.com] |
| YMR281W | Research Genetics, Inc. [world wide web.resgen.com] |
| YMR298W | Research Genetics, Inc. [world wide web.resgen.com] |
| YNL258C | Research Genetics, Inc. [world wide web.resgen.com] WO 98/44135. |
| YOL026C | Research Genetics, Inc. [world wide web.resgen.com] |
| YPL126W | Research Genetics, Inc. [world wide web.resgen.com] |
| YDR240C | RNA, 4:374–393. |
| YJR141W | WO 98/44135 |
| YLL003W | WO 98/44135 |
| YNL038W | WO 98/44135 |
| YBR049C | Yeast, 10:771–787. |
| YGL228W | Yeast, 11:25–32. |
| YNL194C | Yeast, 13:1181–1194. |
| YJR041C | Yeast, 13:1181–1194. |
| YJR046W | Yeast, 13:1181–1194. |
| YML091C | Yeast, 14:77–87. |

Identification of Fungal Genes Present in Pathogenic Fungi

The present invention encompasses fungal-specific genes that are important for growth and are present in at least one pathogenic fungal species. A pathogenic fungal species is any species capable of causing infection and/or infestation in animals or plants. Pathogenic fungal species include without limitation Saccharomyces, Candida, Aspergillus, Schizosaccharomyces, Histoplasma, Coccidioides, Blastomyces, and Cryptococcus species. The presence of a gene in a pathogenic fungal species may be determined by any means known in the art. For example, a fungal-specific gene that has been shown to be important for growth in one fungal species may be used as a probe to identify homologous genes in other fungal species. Homology may be determined experimentally. Alternatively, homology analysis may be performed computationally, as described above, when relevant DNA or polypeptide sequences are known. In practicing the present invention, a gene that shares at least about 70% DNA sequence homology at the nucleotide level with the genome of a pathogenic fungal species is considered to be present in that pathogenic fungal species.

The determination that a nucleic acid is present in a pathogenic fungal species may be achieved using any technique known in the art. Appropriate techniques include without limitation hybridization of gene-specific probes to immobilized genomic DNA, hybridization of labeled genomic DNA to immobilized specific genes or fragments of genes, hybridization to colonies or plaques representing genomic or cDNA libraries, polymerase chain reaction (PCR) using degenerate primers or gene-specific primers and genomic DNA as template, genetic or biochemical complementation, antibody cross-reactivity.

In applying these techniques, conditions are established that discriminate different levels of homology between probe and template. For example, for hybridization of a probe to immobilized DNA (whether in a Southern blot, dot blot, or colony hybridization format), varying the SSC concentration in the buffer allows the detection of hybrids having different levels of homology (1×SSC is 0.15 M NaCl-0.015 M Na citrate). In a wash buffer containing 6M urea and 0.4% sodium dodecyl sulfate, the presence of 2×SSC, 0.5×SSC, 0.1×SSC, and 0.05×SSC allows the formation of hybrids having threshold homologies of at least 55%±5%, 65%±5%, 75%±5%, and >85%, respectively.

Preferably, once a nucleic acid has been identified in a pathogenic fungal species by hybridization or PCR, the DNA sequence of the nucleic acid is determined directly. If the target nucleic acid contains introns (as is common in Aspergillus species), a cDNA library is probed in parallel to the genomic DNA to identify contiguous protein-coding sequences derived from the target nucleic acid.

As an alternative to DNA-DNA hybridization, sequences derived from *S. cerevisiae* genes that had been identified as fungal-specific and important for growth by the methods described above were used to query available nucleotide or protein sequence databases containing sequences of fungal pathogens. An *S. cerevisiae* protein was judged to have an ortholog in a fungal pathogen if upon alignment of predicted protein sequences by the BLAST alogrithm, the global alignment of the two proteins had a sequence identity of 30% or greater. In addition, the presumptive ortholog was determined to have the highest homology to the query protein in the entire *S. cerevisiae* proteome.

It will be understood that some methods that detect homologous sequences may result in the identification or isolation of only a portion of the entire protein-coding sequence of a particular fungal-specific nucleic acid. The entire protein-coding sequence can be isolated and identified, for example, by using an isolated nucleic acid encoding the known portion of the sequence, or fragments thereof, to prime a sequencing reaction with genomic DNA as template; this is followed by sequencing the amplified product. The isolated nucleic acid encoding the disclosed sequence, or fragments thereof, can also be hybridized to appropriate genomic libraries to identify clones containing additional complete segments of the protein-coding sequence of which the shorter sequence forms a part. Then, the entire protein-coding sequence, or fragments thereof, or nucleic acids encoding all or part of the sequence, or sequence-conservative or function-conservative variants thereof, may be employed in practicing the present invention.

In a similar manner, additional sequences derived from the 5' and 3' flanking regions of sequence encoding the protein, including regulatory sequences, may be isolated, and the nucleotide sequence determined.

DNA, Vectors, and Host Cells

In practicing the present invention, many conventional techniques in molecular biology, microbiology, and recombinant DNA, are used. Such techniques are well known and are explained fully in, for example, Sambrook et al., 1989, *Molecular Cloning: A Laboratory Manual*, Second Edition, Cold Spring Harbor Laboratory Press, Cold Spring Harbor, New York; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively), and *Guide to Yeast Genetics and Molecular Biology, Meth. Enzymol.* Vol. 194 (Guthrie and Fink, eds.).

The present invention provides a library of nucleic acid sequences encoding polypeptides that comprise targets for antifungal drugs. The libraries also provide probes, primers, and markers which can be used, e.g., in epidemiological studies.

Nucleic acids comprising the antifungal targets disclosed herein or subsequences thereof can be prepared by standard methods using nucleic acid sequence information available in public databases or as determined in the practice of the invention. For example, DNA can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides.

Of course, due to the degeneracy of the genetic code, many different nucleotide sequences can encode particular antifungal target polypeptides or subsequences thereof. The codons can be selected for optimal expression in prokaryotic or eukaryotic systems. Such degenerate variants are also encompassed by this invention.

Insertion of nucleic acids (typically DNAs) derived from the libraries of the invention into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, any site desired may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., 1988, *Science* 239:48. The cleaved vector and the DNA fragments may also be modified if required by homopolymeric tailing.

In certain embodiments, the invention encompasses isolated nucleic acid fragments comprising all or part of the individual nucleic acid sequences encoding antifungal targets. The fragments are at least about 8 nucleotides in length, preferably at least about 12 nucleotides in length, and most preferably at least about 15–20 nucleotides in length. The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

Nucleic acids derived from the libraries of the present invention may be flanked by natural fungal regulatory sequences, or may be associated with heterologous sequences, including promoters, enhancers, response elements, signal sequences, polyadenylation sequences, introns, 5'- and 3'- noncoding regions, and the like. The nucleic acids may also be modified by any means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also included. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

Nucleic acids derived from the libraries of the invention, i.e., encoding antifungal targets, may be cloned into any suitable vectors for replication and/or expression. A large number of vectors, including plasmid and fungal vectors, have been described for replication and/or expression in a variety of eukaryotic and prokaryotic hosts, and may be used for gene therapy as well as for simple cloning or protein expression.

The encoded antifungal target polypeptides may be expressed by using many known vectors, such as pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. The particular choice of vector/host is not critical to the practice of the invention.

Recombinant cloning vectors will often include one or more replication and inheritance systems for cloning or expression, one or more markers for selection in the host, e.g. antibiotic resistance, and one or more expression cassettes. The inserted antifungal target coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, $CaCl_2$ LiCl, LiAc/PEG sphaeroplsting mediated DNA uptake, microinjection, microprojectile, or other established methods.

Appropriate host cells include bacteria, archebacteria, fungi, especially yeast, and plant and animal cells, especially mammalian cells. Of particular interest are *E. coli, B. subtilis, S. aureus, S. cerevisiae, Saccharomyces carlsbergensis, Schizosaccharomyces pombe,* SF9 cells, C129 cells, 293 cells, Neurospora, CHO cells, COS cells, HeLa cells, and immortalized mammalian myeloid and lymphoid cell lines. Preferred replication and inheritance systems include M13, ColE1, SV40, baculovirus, lambda, adenovirus, ARS/CEN (ARS=autonomously replicating sequence; CEN=centromere) 2 μm ARS and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced fungal-specific peptides and polypeptides.

Advantageously, vectors may also include a transcription regulatory element (i.e., a promoter) operably linked to the antifungal target-encoding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH1) promoter. Suitable promoters for mammalian cells include without limitation viral promoters such as that from Simian Virus 40 (SV40), Rous sarcoma virus (RSV), adenovirus (ADV), and bovine papilloma virus (BPV). Eukaryotic cells may also require terminator sequences, polyA addition sequences and enhancer sequences which increase expression. Sequences which cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or prohormone pro region sequences, may also be included. These sequences are well described in the art.

Nucleic acids encoding wild-type or variant antifungal target polypeptides may also be introduced into cells by recombination events. For example, such a sequence can be introduced into a cell, and thereby effect homologous recombination at the site of an endogenous gene or a sequence with substantial identity to the gene. Other recombination-based methods such as nonhomologous recombinations or deletion of endogenous genes by homologous recombination may also be used.

Nucleic acids derived from the libraries of the present invention find use as templates for the recombinant production of antifungal target peptides or polypeptides.

Antifungal Target Peptides and Polypeptides

Both the naturally occurring and recombinant forms of the antifungal target polypeptides identified using the methods of the present invention may be used for drug screening and development. These polypeptides can advantageously be used, e.g., to screen compounds for binding activity.

Antifungal target polypeptides according to the invention are preferably at least five or more residues in length. Preferably, the polypeptides comprise at least about 12, more preferably at least about 20, and most preferably at least about 30 such residues, up to and including the complete amino acid sequence of the protein. Methods for obtaining these polypeptides are described below. Many conventional techniques in protein biochemistry and immunology are used. Such techniques are well known and are explained in *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.), *Hand-* book of *Experimental Immunology*, 1986, Volumes I-IV (Weir and Blackwell eds.), and *Guide to Protein Purification, Meth. Enzymol.* Vol. 182.

Nucleic acids comprising protein-coding sequences (see below) can be used to direct the expression of fungal-specific polypeptides in intact cells or in cell-free transcription/translation or translation systems. The known genetic code, tailored if desired for more efficient expression in a given host organism, can be used to synthesize oligonucleotides encoding the desired amino acid sequences. The phosphoramidite solid support method of Matteucci et al., 1981, *J. Am. Chem. Soc.* 103:3185, the method of Yoo et al., 1989, *J. Biol. Chem.* 764:17078, or other well known methods can be used for such synthesis. The resulting oligonucleotides can be inserted into an appropriate vector and expressed in a compatible host organism.

The polypeptides of the present invention, including function-conservative variants of the disclosed ORFs, may be isolated from wild-type or mutant fungal cells, or from heterologous organisms or cells (including, but not limited to, bacteria, fungi, insect, plant, and mammalian cells) including fungal cells into which a fungal-derived protein-coding sequence has been introduced and expressed. Furthermore, the polypeptides may be part of recombinant fusion proteins.

Polypeptides may be chemically synthesized by commercially available automated procedures, including, without limitation, exclusive solid phase synthesis, partial solid phase methods, fragment condensation or classical solution synthesis. The polypeptides are preferably prepared by solid phase peptide synthesis as described by Merrifield, 1963, *J. Am. Chem. Soc.* 85:2149.

Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the fungal protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a fungal protein or against peptides derived therefrom can be used as purification reagents. Other purification methods are possible.

The present invention also encompasses derivatives and homologues of antifungal target polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Fungal-Specific Antibodies

The present invention encompasses antibodies that specifically recognize fungal-derived immunogenic components, in particular immunogenic components found only in pathogenic fungi. Such antibodies can be used conventionally, e.g., as diagnostic reagents, as reagents for purification of fungal cells and components, or for passive immunotherapy.

Fungal-specific antibodies according to the present invention include polyclonal and monoclonal antibodies. The antibodies may be elicited in an animal host by immunization with fungal-derived immunogenic components or may be formed by in vitro immunization (sensitization) of immune cells. The immunogenic components used to elicit the production of antibodies may be isolated from fungal cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including Fab' and F(ab)$_2$ fragments of antibodies.

The immunogenic components of this invention are useful as antigens for preparing antibodies by standard methods. These antibodies, whether polyclonal or monoclonal, can be used, e.g., in an immobilized form bound to a solid support by well known methods, to purify the immunogenic components by immunoaffinity chromatography.

It is well known in the art that epitopes generally contain at least about five amino acid residues, Ohno et al., 1985, *Proc. Natl. Acad. Sci. USA* 82:2945. Therefore, the immunogenic components of this invention will typically comprise at least five amino acid residues of the sequence of the complete polypeptide chains. Preferably, they will contain at least 7, and most preferably at least about 10 amino acid residues or more to ensure that they will be antigenic. Whether a given component is immunogenic can readily be determined by routine experimentation. Such immunogenic components can be produced by proteolytic cleavage of larger polypeptides or by chemical synthesis or recombinant technology and are thus not limited by proteolytic cleavage sites.

Hybridomas of the invention used to make monoclonal antibodies against the immunogenic components of the invention are produced by well-known techniques. Usually, the process involves the fusion of an immortalizing cell line with a B-lymphocyte that produces the desired antibody. Alternatively, non-fusion techniques for generating immortal antibody-producing cell lines are possible, and come within the purview of the present invention, e.g., virally-induced transformation, Casali et al., 1986, *Science* 234:476. Immortalizing cell lines are usually transformed mammalian cells, particularly myeloma cells of rodent, bovine, and human origin. Most frequently, rat or mouse myeloma cell lines are employed as a matter of convenience and availability.

Hybridomas are selected by standard procedures, such as HAT (hypoxanthine-aminopterin-thymidine) selection. From among these hybridomas, those secreting the desired antibody are selected by assaying their culture medium by standard immunoassays, such as immunoblotting, ELISA (enzyme-linked immunosorbent assay), RIA (radioimmunoassay), or the like. Antibodies are recovered from the medium using standard protein purification techniques, Tijssen, 1985, *Practice and Theory of Enzyme Immunoassays*, Elsevier, Amsterdam.

Diagnostic Applications

The present invention encompasses compositions, methods, and kits useful in clinical settings for the qualitative or quantitative diagnosis of fungal infection. These applications typically utilize nucleic acids, peptides/polypeptides, or antibodies specific for fungal components. The fungal components may be shared by all or some species of fungi or may be restricted to pathogenic fungi. The methods may also be used to detect specific fungal strains and to detect new fungal strains in a patient, in particular a human patient.

Antibody-based Diagnostic Methods:

The invention provides methods for detecting fungal antigenic components in a biological sample, which methods comprise the steps of: (i) contacting a sample suspected to contain a fungal-derived antigenic component with an antibody specific for a fungal antigen, extracellular or intracellular, under conditions in which a stable antigen-antibody complex can form between the antibody and the fungal antigenic components in the sample; and (ii) detecting any antigen-antibody complex formed in step (i) using any suitable means known in the art, wherein the detection of a complex indicates the presence of fungal antigenic components in the sample. It will be understood that assays that utilize antibodies directed against sequences previously unidentified, or previously unidentified as being fungal-specific, which sequences are disclosed herein, are within the scope of the invention.

Many immunoassay formats are known in the art, and the particular format used is determined by the desired application. An immunoassay may use, for example, a monoclonal antibody directed against a single fungal epitope, a combination of monoclonal antibodies directed against different epitopes of a single fungal-derived antigenic component, monoclonal antibodies directed towards epitopes of different antigens, polyclonal antibodies directed towards the same antigen, or polyclonal antibodies directed towards different antigens. Protocols may also, for example, use solid supports, or may involve immunoprecipitation.

Typically, immunoassays use either a labeled antibody or a labeled antigenic component (e.g., that competes with the antigen in the sample for binding to the antibody). Suitable labels include without limitation enzyme-based, fluorescent, chemiluminescent, radioactive, or dye molecules. Assays that amplify the signals from the probe are also known, such as, for example, those that utilize biotin and avidin, and enzyme-labeled immunoassays, such as ELISA assays.

Kits suitable for antibody-based diagnostic applications typically include one or more of the following components:
  (i) Anti-fungal antibodies: The antibodies may be pre-labeled; alternatively, the antibody may be unlabelled and the ingredients for labeling may be included in the kit in separate containers, or a secondary, labeled antibody is provided; and
  (ii) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

In another embodiment, the invention provides methods for diagnosis of fungal infection by detection of fungal antibodies that have been produced in the patient in response to exposure to a fungus. The method is carried out by (i) contacting a sample suspected to contain anti-fungal antibodies with a fungal-derived antigenic component under conditions in which a stable antigen-antibody complex can form between the antigenic component and anti-fungal antibodies in the sample; and (ii) detecting any antigen-antibody complexes formed in step (i) using any suitable means known in the art. The amount of anti-fungal antibodies forming the antigen-antibody complex may be measured directly. Alternatively, the presence and amount of anti-fungal antibodies in the biological sample may be deduced by measuring the competitive effect of the biological sample on the binding of a known amount of antibody to a known amount of ligand. Methods for direct and competitive immunoassays are well-known in the art.

Nucleic-acid-based Diagnostic Methods:

The invention provides methods for detecting fungal-derived nucleic acids in a sample, such as in a biological sample, which methods comprise the steps of: (i) contacting a sample suspected to contain a fungal-derived nucleic acid with one or more fungal-derived nucleic acid probes under conditions in which hybrids can form between any of the probes and fungal nucleic acid in the sample; and (ii) detecting any hybrids formed in step (i) using any suitable means known in the art, wherein the detection of hybrids indicates the presence of the fungal nucleic acid in the sample.

Fungal-specific nucleic acids useful as probes in diagnostic methods include oligonucleotides at least about 8 nucleotides in length, preferably at least about 12 nucleotides in length, and most preferably at least about 15–20 nucleotides in length, that hybridize specifically with one or more fungal strains. Strain-specific nucleic acid probes may also be used, when it is desired to identify specific fungal strains for purposes of determining treatment modalities.

A sample to be analyzed, such as, for example, a biological sample or an environmental sample, may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation or used for PCR.

PCR based diagnostic kits are also contemplated and are encompassed by the invention.

Kits suitable for nucleic acid-based diagnostic applications typically include the following components:
  (i) Probe DNA: The probe DNA may be pre-labeled; alternatively, the probe DNA may be unlabelled and the ingredients for labeling may be included in the kit in separate containers; and
  (ii) Hybridization reagents: The kit may also contain other suitably packaged reagents and materials needed for the particular hybridization protocol, including solid-phase matrices, if applicable, and standards.

Screening for Antifungal Agents

Isolated genes encoding antifungal target polypeptides are used as the basis for low-throughput and high-throughput assays to identify antifungal agents. Such agents include both fungicidal and fungistatic agents. The inhibitory agents may comprise nucleic acids, particularly antisense oligonucleotides; peptides; oligosaccharides; lipids; derivatives of any of the foregoing, or other molecules.

The inhibitory agents may be identified using methods well-known in the art, such as, for example, by screening chemical or natural product libraries for the ability to bind to, and/or inhibit or alter the function of the nucleic acids or polypeptides of the invention. Such compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, NJ), Brandon Associates (Merrimack, NH), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (NC), or are readily producible. Additionally, natural and synthetically produced libraries and compounds are readily modified through conventional chemical, physical, and biochemical means (Blondelle et al., 1996, TibTech 14:60).

Inhibitory agents may be identified by screening in high through put assays against fungal-specific targets. Such assays include without limitation genetic or overexpression assays and ligand binding assays. Both overexpression and ligand binding assays allow for the high through put screening of a large number of targets. Since not all targets are suitable for overexpression or ligand binding assays, other types of assays, e.g., cell-free biochemical assays, are also contemplated for use. It will be appreciated by those skilled in the art that different types of assays can be used to detect different types of inhibitors.

Several methods of automated assays have been developed in recent years so as to permit screening of tens of thousands of compounds in a short period of time. Such high through put screening methods are particularly preferred. The use of high through put screening assays to test for inhibitors is greatly facilitated by the availability of large amounts of purified polypeptides, as provided by the invention.

Overexpression Assays

Overexpression assays (described in U.S. Pat. Nos. 4,980,281 and 5,688,655) are based on the premise that overproduction of a protein would lead to a higher level of resistance to compounds that selectively interfere with the function of that protein. Typically, a yeast strain is constructed that contains the gene of interest under the control of an inducible promoter. Identification of useful inhibitory agents using this type of assay is based on a comparison of the activity of a test compound in inhibiting growth and/or viability of this strain under both inducing and non-inducing conditions. This type of screening method may be used to identify compounds that interfere with the function of virtually any type of protein, including without limitation enzymes, receptors, DNA- or RNA-binding proteins, or any proteins that are directly or indirectly involved in regulating cell growth.

The method involves constructing a nucleic acid vector that directs increased expression of a particular target nucleic acid. The vector is then used to transform host cells, which are subsequently grown under both non-inducing and inducing conditions (conditions A and B, respectively). Large numbers of compounds (or crude substances which may contain active compounds) are screened for their effect on growth under these two conditions. Agents that interfere with the function of the target should inhibit viability under both conditions. It should be possible, however, to titrate out the inhibitory effect of the compound in the overexpressing strain. That is, if the compound affects the particular target that is being tested, it should be possible to inhibit growth under condition A at a concentration that allows the strain to grow under condition B.

Alternatively, the overexpression assay may be carried out in such a way that a comparison is made between the growth, with and without inhibitory compounds, of several independent transformants overexpressing different, unrelated, target polypeptides. If an inhibitory compound exists that selectively targets one of the overexpressed polypeptides, then overexpression of that polypeptide may confer a detectable level of resistance, as measure by increased culture growth. Whereas, overexpression of heterologous, unrelated proteins will not ameliorate the growth inhibitory effects of that specific compound.

Ligand-binding Assays

Some of the targets according to the invention may have functions that have not yet been identified. Ligand-binding assays are useful to identify inhibitor compounds that interfere with the function of a particular target, even when that function is unknown. Furthermore, useful targets may include polypeptides that are not essential for growth or viability per se but serve as binding sites for toxic drugs or in any other way, can be used to target therapeutic agents to cells.

These assays are designed to detect binding of test compounds to particular targets. The detection may involve direct measurement of binding. Alternatively, indirect indications of binding may involve stabilization of protein structure or disruption of a biological function. Non-limiting examples of useful ligand-binding assays are detailed below.

A useful method for the detection and isolation of binding proteins is the Biomolecular Interaction Assay (BIAcore) system developed by Pharmacia Biosensor and described in the manufacturer's protocol (LKB Pharmacia, Sweden). The BIAcore system uses immobilized proteins, such as, e.g., GST-fusion proteins that are bound to a sensor chip via affinity purified anti-GST antibodies. The sensor utilizes surface plasmon resonance which is an optical phenomenon that detects changes in refractive indices. In accordance with the practice of the invention, a protein of interest is coated onto a chip and test compounds are passed over the chip. Binding is detected by a change in the refractive index (surface plasmon resonance).

A type of ligand binding assay, currently undergoing development, is based on the fact that proteins containing mitochondrial targeting signals are imported into isolated mitochondria in vitro (Hurt et al., 1985, *Embo J.* 4:2061–2068; Eilers and Schatz, *Nature*, 1986, 322:228–231). In a mitochondrial import assay, expression vectors are constructed in which nucleic acids encoding particular target proteins are inserted downstream of sequences encoding mitochondrial import signals. The chimeric proteins are synthesized and tested for their ability to be imported into isolated mitochondria in the absence and presence of a test compound. A test compound that binds to the target protein should inhibit its uptake into isolated mitochondria in vitro.

Another ligand-binding assay is the yeast two-hybrid system (Fields and Song, 1989, *Nature* 340:245–246; U.S. Pat. No. 5,283,173). The two-hybrid system relies on the reconstitution of transcription activation activity by association of the DNA-binding and transcription activation domains of a transcriptional activator through protein-protein interaction. The yeast GAl4 transcriptional activator may be used in this way, although other transcription factors have been used. These other systems are well known in the art. To carryout the two-hybrid assay, the GAL4 DNA-binding domain and the transcription activation domain are expressed, separately, as fusions to potential interacting polypeptides. If the two, coexpressed fusion proteins are targeted to the nucleus and interact, activation of a reporter gene (e.g. LacZ) produces a detectable phenotype. Related, in vivo, methods such as the three-hybrid (Licitra and Liu, 1996, *Proc. Natl. Acad. Sci. USA* 93:12817–12821), and reverse two-hybrid (Vidal et al., 1996, *Proc. Natl. Acad. Sci. USA* 93:10315–10320) may serve as alternative approaches.

Ligand-binding assay involving scintillation proximity assays (SPA, described in U.S. Pat. No. 4,568,649) may also be of use as can the binding assay described in Fodor et al., 1991, *Science* 251:767–773, which involves testing the binding affinity of test compounds for a plurality of defined polymers synthesized on a solid substrate, may also be useful.

Therapeutic Applications

Vaccines:

The invention provides polypeptide and nucleic acid sequences that are contemplated for use as components of vaccines. Polypeptides useful as immunogenic components are those that elicit antibodies and/or protective immunity after introduction into a host animal. The sequences listed in Table 1, as well as homologous sequences of pathogenic strains including but not limited to *C. alvicans* and *A. fumigatus*, that are contemplated for use as components of vaccines are those that elicit a humoral and/or cellular immune response that is (i) specific to externally-disposed fungal antigens and (ii) capable of neutralizing fungal infectivity following contact with antibodies and/or immune cells specific to the fungal immunogenic component. Most preferably, the sequence is capable of eliciting an immune response having the above-described characteristics when incorporated in a pharmaceutically acceptable vaccine formulation.

Methods for determining the immunogenic capability of the disclosed sequences and the characteristics of the resulting sequence-specific antibodies and immune cells are well-known in the art. For example, antibodies elicited in response to a particular polypeptide can be tested for the ability to bind and agglutinate other fungal cells. In this manner, it is possible for one of ordinary skill in the art to identify the most preferred polypeptides for use in vaccines.

The present invention encompasses vaccines effective in prevention or lessening of fungal-mediated disease. Prevention or lessening of disease is understood to mean the amelioration of any symptoms, including a lessening of the dosage of an antifungal medication used to treat the disease. An "effective" vaccine is one that exhibits both efficacy and safety.

In one embodiment, vaccines according to the invention comprise one or more fungal-derived immunogenic polypeptide components. The polypeptides, or peptides derived therefrom, may be isolated from their native host cells, may be chemically synthesized, or may be isolated from recombinant host cells. Combination vaccines may include immunogenic components derived from more than one pathogen. DNA vaccines may be prepared in which one or more DNA sequences encoding the desired immunogenic components are incorporated into a suitable vector or virus, which is formulated into a vaccine preparation. The immunogenic components or nucleic acids may be incorporated into liposomes, or encapsulated in peptide-, protein-, or polysaccharide-based microcapsules or microspheres prior to administration, using means that are known in the art.

There are many protocols for the preparation of vaccines known in the art. Typically, vaccines are prepared as injectables, either as liquid solutions or suspensions. Solid forms suitable for dissolving or suspending in liquid prior to injection may also be prepared. The preparation may also be emulsified, or the protein encapsulated in liposomes. The active immunogenic ingredients may be mixed with excipients, such as, for example, water, saline, dextrose, glycerol, ethanol, or the like, and combinations thereof. In addition, if desired, the vaccine may contain minor amounts of auxiliary substances such as wetting or emulsifying agents, pH buffering agents, and/or adjuvants which enhance the effectiveness of the vaccine.

Oral formulations include conventional excipients such as, for example, pharmaceutical grades of mannitol, lactose, starch, magnesium stearate, sodium saccharine, cellulose, magnesium stearate, sodium saccharine, cellulose, magnesium carbonate, and the like. These compositions take the form of solutions, suspensions, tablets, pills, capsules, sustained release formulations or powders and contain 10%–95% (w/w) of active ingredient, preferably 25%–70% (w/w).

The immunogenic components may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salt formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines may be administered by subcutaneous, intramuscular, intravenous, oral, intradermal, or intranasal routes. Dosages may range from about 5 $\mu$g to about 2 mg per dose, and a single or multiple dosage regimen may be utilized. The amounts administered, number of administrations, and schedule of administrations can be determined empirically, such as, for example, by establishing a matrix of dosages and frequencies and comparing a group of experimental units or subjects to each point in the matrix.

Assessment of Vaccine Efficacy: The efficacy of the vaccines of the present invention can be assessed in experimental animals using methods well-known in the art. For example, at an appropriate time following vaccination, preferably 1–2 months vaccinates and control animals are challenged with a infective dose of fungi sufficient to produce clinically detectable signs of infection within a manageable time, such as, e.g., 1 week. Clinical signs of infection are monitored, and body fluids are cultured for fungal organisms. A statistical comparison of clinical signs and recovery of the fungus in vaccinates versus controls is performed to assess the efficacy of a particular vaccine preparation or administration regimen.

Pharmaceuticals:

Compounds identified as binding to a polypeptide encoded by a member of the nucleic acid libraries of the invention or otherwise interfering with its function are potentially useful as antifungal agents for use in pharmaceutical and/or agricultural compositions.

Once a particular test compound has been identified as a candidate antifungal agent, it is tested for two properties: (i) the ability to inhibit fungal growth; and (ii) a lack of effect on different animals. Fungal viability is measured by any method well-known in the art, such as, but not limited to, monitoring the optical density of a liquid culture as a function of cell concentration or by quantifying colony formation on agar or cell viability by exclusion of dyes etc. The potential toxicity of an agent for, e.g., mammalian cells is measured by monitoring its effect in a conventional mammalian cell culture, such as, for example, L cells. Agents that exhibit antifungal activity and lack of toxicity for animal cells may be used in antifungal treatments.

Pharmaceutical formulations suitable for antifungal therapy comprise the antifungal agent in conjunction with one or more biologically acceptable carriers. Suitable biologically acceptable carriers include, but are not limited to, phosphate-buffered saline, saline, deionized water, or the like. Preferred biologically acceptable carriers are physiologically or pharmaceutically acceptable carriers.

The antifungal compositions include an antifungal effective amount of active agent. Antifungal effective amounts are those quantities of the antifungal agents of the present invention that afford prophylactic protection against fungal infections or which result in amelioration or cure of an existing fungal infection. This antifungal effective amount will depend upon the agent, the location and nature of the infection, and the particular host. The amount can be determined by experimentation known in the art, such as by establishing a matrix of dosages and frequencies and comparing a group of experimental units or subjects to each point in the matrix. The prophylactically and/or therapeutically effective amounts can be administered in one administration or over repeated administrations. Therapeutic administration can be followed by prophylactic administration, once the initial bacterial infection has been resolved.

The antifungal active agents or compositions can be formed into dosage unit forms, such as for example, creams, ointments, lotions, powders, liquids, tablets, capsules, suppositories, sprays, or the like. If the antifungal composition is formulated into a dosage unit form, the dosage unit form may contain an antifungal effective amount of active agent. Alternatively, the dosage unit form may include less than such an amount if multiple dosage unit forms or multiple dosages are to be used to administer a total dosage of the active agent. Dosage unit forms can include, in addition, one or more excipient(s), diluent(s), disintegrant(s), lubricant(s), plasticizer(s), colorant(s), dosage vehicle(s), absorption enhancer(s), stabilizer(s), bactericide(s), or the like.

For general information concerning formulations, see, e.g., Gilman et al. (eds.), 1990, *Goodman and Gilman's: The Pharmacological Basis of Therapeutics*, 8th ed., Pergamon Press; and *Remington's Pharmaceutical Sciences*, 17th ed., 1990, Mack Publishing Co., Easton, Pa.; Avis et al. (eds.), 1993, *Pharmaceutical Dosage Forms: Parenteral Medications*, Dekker, New York; Lieberman et al. (eds.), 1990, Pharmaceutical Dosage Forms: Disperse Systems, Dekker, New York.

The antifungal agents and compositions of the present invention are useful for preventing or treating fungal infections or infestations. Infection prevention methods incorporate a prophylactically effective amount of an antifungal agent or composition. A prophylactically effective amount is an amount effective to prevent fungal infection or infestation and will depend upon the specific fungal strain, the agent, and the host. These amounts can be determined experimentally by methods known in the art and as described above.

The antifungal agents and compositions can be administered topically or systemically. Topical application is typically achieved by administration of creams, ointments, lotions, or sprays as described above. Systemic administration includes both oral and parental routes. Parenteral routes include, without limitation, subcutaneous, intramuscular, intraperitoneal, intravenous, transdermal, and intranasal administration.

The following examples are intended to further illustrate the present invention without limiting its scope.

Example 1

Identification of Antifungal Target Eenes Derived from *S. cerevisiae*

The following experiments were performed to identify antifungal target genes according to the present invention.

1. Fungal-specific Genes

Using the BLAST algorithm, all possible ORFs greater than 180 nucleotides in all six reading frames were identified in the complete genomic sequence of *S. cerevisiae* and were translated into amino acid sequences. The deduced polypeptide sequences were then analyzed for homology to known (both prokaryotic and eukaryotic) protein sequences. More than 2100 *S. cerevisiae* genes were identified as having no known homologues in higher eukaryotes or in bacteria and were designated "fungal-specific" *S. cerevisiae* genes.

2. Fungal Genes Important for Growth

Genetic footprinting was used to identify fungal-specific *S. cerevisiae* genes that are also important for growth. Footprinting was performed in the DBY7286 strain of *S. cerevisiae* using essentially the method disclosed in Smith et al., 1995, *Proc. Natl. Acad. Sci. USA* 92:5479–6433. Briefly, cells were transformed with the pBTy1 plasmid encoding the Ty1 transposon under the control of the GALL promoter. To induce expression of the transposase, and initiate transposition, transformed cells were used to inoculate synthetic complete (SC) medium lacking uracil and containing 2% galactose, and grown for 4 days. Genomic DNA was prepared from this culture (designated the T0 sample). The cells were then cultivated for 20 population doublings in a 10L fermentor containing YPD medium (2% Bacto-peptone, 1% yeast extract, and 2% dextrose) at 28° C. Culture density was kept below $5 \times 10^8$ throughout. Genomic DNA was prepared (designated the T20 sample).

PCR analysis of the footprinting patterns of the genes previously identified as fungal-specific (see above) was performed using conventional techniques. Typically, PCR reactions contained 1 $\mu$g (chromosomal) template DNA; 10 mM Tris-HCl, pH 8.5; 1.5 mM $MgCl_2$; 0.5 $\mu$M each primer (including a fluorescent-labeled gene-specific 24-mer oligonucleotide and an unlabelled Ty1-specific oligonucleotide, designated PBTY1R1, having the sequence 5'AGAGCTCCCGGGATCCTCTACTAAC-3'(SEQ ID No.1)); 250 $\mu$M each dNTP; and 2 units Taq DNA Polymerase in a 50 $\mu$l reaction volume. The reactions were incubated at 93° C., 1 minute; 10 cycles of 92° C., 30 seconds, 67° C., 45 seconds, and 72° C., 2 minutes; and 20 cycles of 92° C., 30 seconds, 62° C., 45 seconds, and 72° C., 2 minutes. The PCR products were analyzed on 12 cm 5% Long Ranger acrylamide gels in 6M urea and 1×TBE. Electrophoresis was at 680 V for 4 hours on an ABI/Perkin-Elmer 377 DNA Sequencer. Data were collected and analyzed using the ABI/Perkin-Elmer GeneScan and Genotyper software packages.

These experiments resulted in the identification of *S. cerevisiae* genes that fall into four categories, from very important for viability (Level 1) to not important for viability (Level 4). 163 genes were identified as Level 1; 133 as Level 2; 192 as Level 3; and the remainder as Level 4 (which included reactions in which the PCR primers failed to support amplification).

3. Genes Present in Pathogenic Fungi

Sequences derived from *S. cerevisiae* genes that had been identified as fungal-specific and important for growth by the methods described above were used as probes to determine if homologues of these genes are present in *C. alvicans* and *A. fumigatus*.

Briefly, genomic DNA was isolated from *C. alvicans* strain C43 and *A. fumigatus* strain ND158 and DNA samples prepared at different concentrations were applied to Zeta Probe GT membranes (Biorad) using a dot-blot apparatus. The membranes were rinsed briefly in 2×SSC, air dried, and baked at 80° C. for 30 minutes under vaccum.

Hybridization was performed using gel-purified PCR products corresponding to the entire open reading frame, obtained by amplification from genomic DNA (*S. cervisiae* strain S288C). Probes were labelled using chemiluminescent moieties (ECL, Amersham). The hybridization solution was ECL Gold hybridization buffer containing 1M NaCl and 5% blocking reagent (Amersham Life Sciences). After prehybridization at 42° C. for 15–60 minutes, hybridization solution containing 20 ng/ml probe was added, and hybridization was allowed to proceed at 40° C. overnight.

Following hybridization, the membranes were washed for 10 minutes at 42° C. in a primary wash buffer containing 6M urea, 0.4% SDS, and either 2×, 0.5×, 0.1×, or 0.05×SSC. Following the primary wash, all membranes were washed for 10 minutes at room temperature in 20×SSC, followed by a final wash for 10 minutes in the primary wash buffer lacking urea and SDS. Finally, chemilumiscent detection was performed according to the manufacturer's instructions. This procedure results in the identification of genes having different relative degrees of homology between *S. cerevisiae* probes and *C. albicans* or *A. fumigatus* sequences.

To determine which genes, identified as fungal-specific and important for growth, were present in fungal pathogens other than *C. albicans* and *A. fumigatus*, hybridization to approximately 6200 open reading frames (ORFs) of *S. cerevisiae* was performed. Membranes containing 6144 *S. cerevisiae* ORFs, individually amplified by PCR and spotted were obtained from Research Genetics, Inc. (Huntsville, Ala.). Genomic DNA from a pathogenic fungal organism was randomly labeled using chemiluminescent moieties and used to probe the immobilized *S. cerevisiae* ORFs.

Genomic DNA from various fungal organisms was isolated by standard methods. The DNA was then purified using Gene Clean (BIO101, Inc., Vista, Calif.) according to the manufacturer's instructions. Following purification, 2–25 $\mu$g of each preparation was sheared by sonication with a Branson Sonifier® (Branson Sonic Power Co., Inc., Danbury, Conn.) according to the following scheme. With the Sonifier® set to 50% pulse and a power setting of "4", four pulses were applied for 5 seconds each using the "pulse" mode and one pulse was applied for 5 sec using the "continuous" mode. Sheared DNA was then analyzed by gel electrophoresis before proceeding. Sonicated, genomic DNA preparations were diluted to 10 ng/$\mu$l in water and labeled (ECL, Amersham, Inc.), the day of use, according to manufacturer's instructions (incubation with glutaraldehyde was extended to at least 30 minutes). Hybridization, washes, and chemiluminescent detection were carried out as described above with the exception that the final wash was 6M urea, 0.4% SDS and 2×SSC. At this level of stringency, genes that share approximately ~55% similarity or greater were detected.

4. Antifungal Targets

The concerted use of the methods described above result in the identification of antifungal target genes, i.e., fungal-specific genes that are important for fungal growth and are present in at least one pathogenic fungal species.

Example 2

Identification of Antifungal Agents Using an Overexpression Assay

The following experiments use individual fungal-specific target genes identified in accordance with the invention to identify antifungal agents.

1. Vector Construction for Over Expression Assay Strain

The multicloning site (MCS) and flanking sequences from pET32a (Novagen) from position 140 nt to position 371 nt was amplified introducing a SpeI site at the 5' end of the fragment and two in-frame stop codons as well as a SacII site at the 3' end of the fragment. The pET32a flanking sequences encode an S-tag (Kim et al., 1993, *Protein Sci.* 2:348) and HisX6-Tag (U.S. Pat. No. 5,310,663) at the amino terminus and a second 6xHis-Tag at the carboxyterminus. The entire fragment was introduced at the SpeI/SacII site of pRS426 (Christianson et al., 1992, *Gene* 110:119–122), a yeast shuttle plasmid encoding β-galactosidase alpha peptide, and containing 2 micron sequences for high copy propagation in yeast, URA3 selectable marker, GAL1 promoter, the pMB1 replicon and AmpR gene from *E. coli*. Two of the available MCS cloning sites (BamHI & EcoRI) within the vector backbone, and another two sites (NcoI & EcoRV) within the URA3 selectable marker were eliminated by site-directed mutagenesis while maintaining the original amino acid sequence where necessary. The 5'-Hisx6-Tag from the pET32a fragment was also eliminated using PCR amplification and replacement. An *S. cerevisiae* CYC1 terminator sequence (262bp; Zaret and Sherman, 1982, *Cell*, 28:583) was amplified and inserted immediately downstream of the MCS-stop codon sequences.

A backup vector containing the constitutive promoter, ADH1, in place of GAL1 is used in situations in which a 1000-fold induction of the target gene is toxic to the host cell. In this strategy, overexpression is provided by a combination of the copy number of the plasmid and the relative strength of the ADH1 promoter.

2. Cloning and Confirmation of Expression

Each fungal-specific target gene is cloned into an overexpression vector which is then used to transform a suitable yeast host, and tested for expression levels by Western analysis using the N- and C-terminal tags.

3. Supersensitive Yeast Host

In a preferred embodiment of the invention, a yeast host strain that is sensitive to a wide range of chemical structures is used to express the gene product. Deletion of some genes in an otherwise wild type yeast strain has been shown to result in an enhanced sensitivity to a broad range of known drugs and antifungals. Many of these gene products have previously been identified as transporters or multi-drug efflux pumps. Disruption of ERG4 can enhance sensitivity of a host strain to a variety of chemical structures by 2–8 times that of a wild type strain (Sauer, 1992, *J. Mol. Biol.* 223:911–928). Since the completion of the Saccharomyces genome, numerous additional putative efflux pumps have been identified by sequence analysis. An appropriate yeast strain for use in the invention is constructed by sequentially disrupting several additional transporters. Each resulting strain is then tested for enhanced sensitivity to a wide class of drugs and antifungal compounds.

4. Functionality of Tagged Screening Targets

The use of amino- and carboxy-terminal peptide tags is not a requirement for protein expression, overexpression assay production, or antifungal compound detection. They are included to serve, through the use of specific affinity reagents, in the analysis and verification of expression of a wide variety of cloned target genes. Furthermore, these tags may serve to allow affinity purification of polypeptide targets for in vitro analysis or screening.

In practicing the invention, it is critical that the screening target proteins containing N-terminal and/or C-terminal "tags" be functional. To determine whether an expressed protein is functional in yeast, a haploid strain is first transformed by an expression plasmid containing a tagged protein (marked by URA3). An in vitro generated construction to allow deletion of the gene by homologous recombination (one-step gene disruption) (marked with either a prototrophic or antibiotic resistance gene is then transformed and used to replace the wild type copy of the target gene). If a strain can be recovered containing both a confirmed genomic deletion and the expression plasmid, this indicates that the gene contained in the expression plasmid is capable of rescuing a knockout of the gene and therefore is functional.

In a second method, heterozygous diploid strains of yeast are constructed containing one wild type copy of the gene and one deleted copy of the gene. These strains are transformed with the overexpression plasmid and the transformed strains are sporulated to generate haploids. As above, recovery of strains containing both the genomic deletion and the expression plasmid indicates that the tagged protein is functional in yeast.

5. High Throughput Screening

The first phase of a typical high-throughput assay involves identifying any natural products or synthetic compounds that have antifungal activity against a supersensitive *S. cerevisiae* strain, which has been engineered to be sensitive to a broad range of antifungal compounds at low levels (such as might be expected in a natural product extract). In this phase, the supersensitive yeast strain is exposed to a variety of culture broths, extracts, synthetic compounds, etc., to identify those that inhibit growth.

In the second phase, the same supersensitive yeast strain is individually transformed with plasmids containing different target genes under the control of an inducible promoter. Each transformed strain is incubated under inducing contitions, exposed to antifungal agents and their growth compared. Rescue is evident when overexpression of a particular gene allows growth in the presence of an antifungal agent, while overexpression of a different non-target related gene does not.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

species, other fungal species, or higher eukaryotic species, wherein substantial homology is indicated by a BLAST P(N) score of less than or equal to $10^{-5}$, and wherein BLAST analysis is performed using a scoring matrix selected from the group consisting of BLOSSUM 62 and PAM 120, and a filtering program selected from the group consisting of SEG and XNU;

(b) assessing whether the nucleic acid is important for growth or viability of the fungal species from which it is derived; and wherein a fungal-derived nucleic acid which serves as a useful target for treatment of fungal diseases is identified as one which is (i) important for fungal growth or viability; (ii) does not share said substantial sequence homology with nucleic acid sequences present in any bacterial species and does not share said substantial sequence homology with nucleic acid sequences present in any higher eukaryotic species; and (iii) shares said substantial sequence homology with a nucleic acid sequence present in at least one pathogenic fungal species.

2. The method according to claim 1, wherein the assessing step (b) is determined by deleting or disrupting the nucleic acid of the fungal species.

3. The method according to claim 1, wherein the assessing step (b) is determined by transposon-mediated insertional mutagenesis of the fungal species.

4. The method according to claim 1, wherein the nucleic acid shares said substantial sequence homology with a nucleic acid sequence present in a Candida fungal species.

5. The method according to claim 1, wherein the nucleic acid shares said substantial sequence homology with a nucleic acid sequence present in an Aspergillus fungal species.

6. The method according to claim 1, wherein the nucleic acid shares said substantial sequence homology with a nucleic acid sequence present in a Saccharomyces fungal species.

7. The method according to claim 6, wherein the nucleic acid shares said substantial sequence homology with a nucleic acid sequence present in *Saccharomyces cerevisiae*.

8. A method for identifying a fungal-derived nucleic acid that is useful as a target for treatment of fungal diseases comprising:

(a) determining if the nucleic acid shares at least 55%±5% homology with nucleic acids present in bacterial

What is claimed is:

1. A method for identifying a fungal-derived nucleic acid that is useful as a target for treatment of fungal diseases comprising:

(a) determining if the nucleic acid shares substantial homology with nucleic acids present in bacterial species, other fungal species, or higher eukaryotic species, wherein said homology is determined by nucleic acid hybridization;

(b) assessing whether the nucleic acid is important for growth or viability of the fungal species from which it is derived; and wherein a fungal-derived nucleic acid which serves as a useful target for treatment of fungal diseases is identified as one which is (i) important for fungal growth or viability; (ii) does not share said sequence homology with nucleic acid sequences present in any bacterial species and does not share said substantial sequence homology with nucleic acid sequences present in any higher eukaryotic species; and (iii) shares said sequence homology with a nucleic acid sequence present in at least one pathogenic fungal species.

9. The method according to claim 8, wherein the assessing step (b) is determined by deleting or disrupting the nucleic acid of the fungal species.

10. The method according to claim 8, wherein the assessing step (b) is determined by transposon-mediated insertional mutagenesis of the fungal species.

11. The method according to claim 8, wherein the nucleic acid shares said sequence homology with a nucleic acid sequence present in a Candida fungal species.

12. The method according to claim 8, wherein the nucleic shares said sequence homology with a nucleic acid sequence present in an Aspergillus fungal species.

13. The method according to claim 8, wherein the nucleic acid shares said sequence homology with a nucleic acid sequence present in a Saccharomyces fungal species.

14. The method according to claim 13, wherein the nucleic acid shares said sequence homology with a nucleic acid sequence present in *Saccharomyces cerevisiae*.

* * * * *